(12) United States Patent
Wu et al.

(10) Patent No.: US 11,540,801 B2
(45) Date of Patent: Jan. 3, 2023

(54) AUTOMATING A MEDICAL ENVIRONMENT

(71) Applicant: SHANGHAI UNITED IMAGING INTELLIGENCE CO., LTD., Shanghai (CN)

(72) Inventors: Ziyan Wu, Lexington, MA (US); Srikrishna Karanam, Brighton, MA (US); Meng Zheng, Cambridge, MA (US); Abhishek Sharma, Boston, MA (US); Ren Li, Cambridge, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 65 days.

(21) Appl. No.: 17/081,381

(22) Filed: Oct. 27, 2020

(65) Prior Publication Data

US 2022/0125400 A1    Apr. 28, 2022

(51) Int. Cl.
*A61B 6/00* (2006.01)
*A61B 6/10* (2006.01)
*G06N 3/02* (2006.01)

(52) U.S. Cl.
CPC .............. *A61B 6/545* (2013.01); *A61B 6/102* (2013.01); *A61B 6/463* (2013.01); *A61B 6/466* (2013.01); *A61B 6/5211* (2013.01); *G06N 3/02* (2013.01)

(58) Field of Classification Search
None
See application file for complete search history.

(56) References Cited

U.S. PATENT DOCUMENTS

| | | | | |
|---|---|---|---|---|
| 5,902,239 | A * | 5/1999 | Buurman | G06T 3/0006 606/130 |
| 2019/0298277 | A1* | 10/2019 | Zhang | A61B 90/13 |
| 2020/0004342 | A1* | 1/2020 | Isaacs | A61B 6/5241 |
| 2020/0297444 | A1* | 9/2020 | Camarillo | G16H 30/40 |
| 2021/0201476 | A1* | 7/2021 | Prasad | G06T 5/007 |

* cited by examiner

*Primary Examiner* — Hoon K Song
(74) *Attorney, Agent, or Firm* — Zhong Law, LLC

(57) ABSTRACT

Systems, methods and instrumentalities are described herein for automating a medical environment. The automation may be realized using one or more sensing devices and at least one processing device. The sensing devices may be configured to capture images of the medical environment and provide the images to the processing device. The processing device may determine characteristics of the medical environment based on the images and automate one or more aspects of the operations in the medical environment. These characteristics may include, e.g., people and/or objects present in the images and respective locations of the people and/or objects in the medical environment. The operations that may be automated may include, e.g., maneuvering and/or positioning a medical device based on the location of a patient, determining and/or adjusting the parameters of a medical device, managing a workflow, providing instructions and/or alerts to a patient or a physician, etc.

18 Claims, 8 Drawing Sheets

AUTOMATING A MEDICAL ENVIRONMENT

BACKGROUND

Medical procedures are complicated operations requiring a high level of concentration, precision, and coordination. Presently, most of the operations taking place in a medical environment are carried out manually. For instance, during surgery, medical staff not only have to focus on executing protocols and observing conditions of the patient, they must also attend to tools and equipment (e.g., lighting, X-ray scanner, etc.) and be generally cognizant of the operating environment to ensure that the tools and equipment are within reach when needed and the movement of one tool or device does not interfere with the ongoing procedure or collide with other tools or devices in the environment. Furthermore, a patient's physical characteristics, positions, and/or movements during a procedure may require continuously adjustments of the parameters, configurations and/or settings of medical devices (e.g., such as an X-ray scanner) so that they may adapt to the specific conditions of the patient. Performing these tasks manually not only impose additional burdens on the medical staff, the manual work also lacks accuracy and consistency and is difficult to monitor or verify. Accordingly, it is highly desirable to automate aspects of the operations in a medical environment to relieve the burden on medical professionals as well as to enhance the safety, efficiency, and effectiveness of the operations.

SUMMARY

Described herein are systems, methods and instrumentalities associated with automating a medical environment. A system as described herein may comprise one or more sensing devices and at least one processing device communicatively coupled to the one or more sensing devices. The one or more sensing devices may be configured to capture images of the medical environment, where the images may be associated with respective image coordinate systems while the medical environment may be associated with a world coordinate system. Each of the one or more sensing devices may include a two-dimensional (2D) visual sensor configured to capture 2D images of the medical environment or a three-dimensional (3D) visual sensor configured to capture 3D images of the medical environment. The at least one processing device may be configured to receive all or a subset of the images captured by the one or more sensing devices, identify one or more persons or one or more objects in the received images (e.g., using an artificial neural network such as a convolutional neural network), and determine respective locations of the one or more persons or the one or more objects in the medical environment based on respective locations of the one or more persons or the one or more objects in the received images.

The at least one processing device may be configured to determine the respective locations of the one or more persons or the one or more objects in the medical environment based at least on respective spatial relationships between the world coordinate system and the image coordinate systems associated with the received images. In accordance with the determined locations of the one or more persons or the one or more objects in the medical environment, the at least one processing device may generate information for controlling a medical device (e.g., at least a part of the medical device) located in the medical environment and transmit the information generated for controlling the medical device to a receiving device. For example, the one or more objects detected in the medical environment may include the medical device, the one or more persons detected in the medical environment may include a patient, and the information generated by the at least one processing device may include a command to move the medical device towards the patient.

In one or more embodiments, the information generated by the at least one processing device may include navigation instructions that prevent the medical device from colliding with the other persons or objects detected in the received images while the medical device moves towards the patient. In one or more embodiments, the information generated by the at least one processing device may include a plot of a movement path of the medical device towards the patient. In one or more embodiments, the images received by the at least one processing device may comprise an image of a patient in the medical environment and the at least one processing device may be configured to generate a parametric human model of the patient based on the image of the patient and further determine the scan area or the surgical area of the patient based on the parametric human model. The at least one processing device may then generate and transmit instructions to move the medical device towards the determined scan or surgical area of the patient. In one or more embodiments, the one or more objects detected in the images received by the at least one processing device may include a radiation source and the at least one processing device may be configured to determine respective radiation exposures of the one or more persons detected in the received images based on the respective locations of the radiation source and the one or more persons determined by the at least one processing device. In one or more embodiments, the at least one processing device may be further configured to determine a phase of a medical procedure being performed in the medical environment based on the one or more persons or the one or more objects detected in the received images and/or information acquired by the at least one processing device regarding various phases of the medical procedure.

The at least one processing device is configured to determine the respective spatial relationships between the world coordinate system and the image coordinate systems based on images of one or more markers located in the medical environment that are captured by the one or more sensing devices. For example, the at least one processing device may be configured to determine respective coordinates of the one or more markers in the image coordinate system associated with each of the images of the one or more markers, determine respective coordinates of the one or more markers in the world coordinate system, and determine a rotation and a translation between the world coordinate system and the image coordinate system associated with each of the images of the one or more markers based on the respective coordinates of the one or more markers in the image coordinate system and the respective coordinates of the one or more markers in the world coordinate system. Further, when one or more of the sensing devices comprise 2D visual sensors, the at least one processing device may be configured to determine a depth of a person or an object detected in a first 2D image captured by a first sensing device based on the first 2D image and a second 2D image captured by a second sensing device.

Each of the one or more sensing devices described herein may comprise a communication circuit and each sensing device may be configured to communicate with at least one other sensing device via the communication circuit. The medical device described herein may comprise an X-Ray scanner such as an X-ray scanner having a C-shaped arm. The receiving device described herein may comprise the medical device or a control unit (e.g., a remote control unit) of the medical device.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
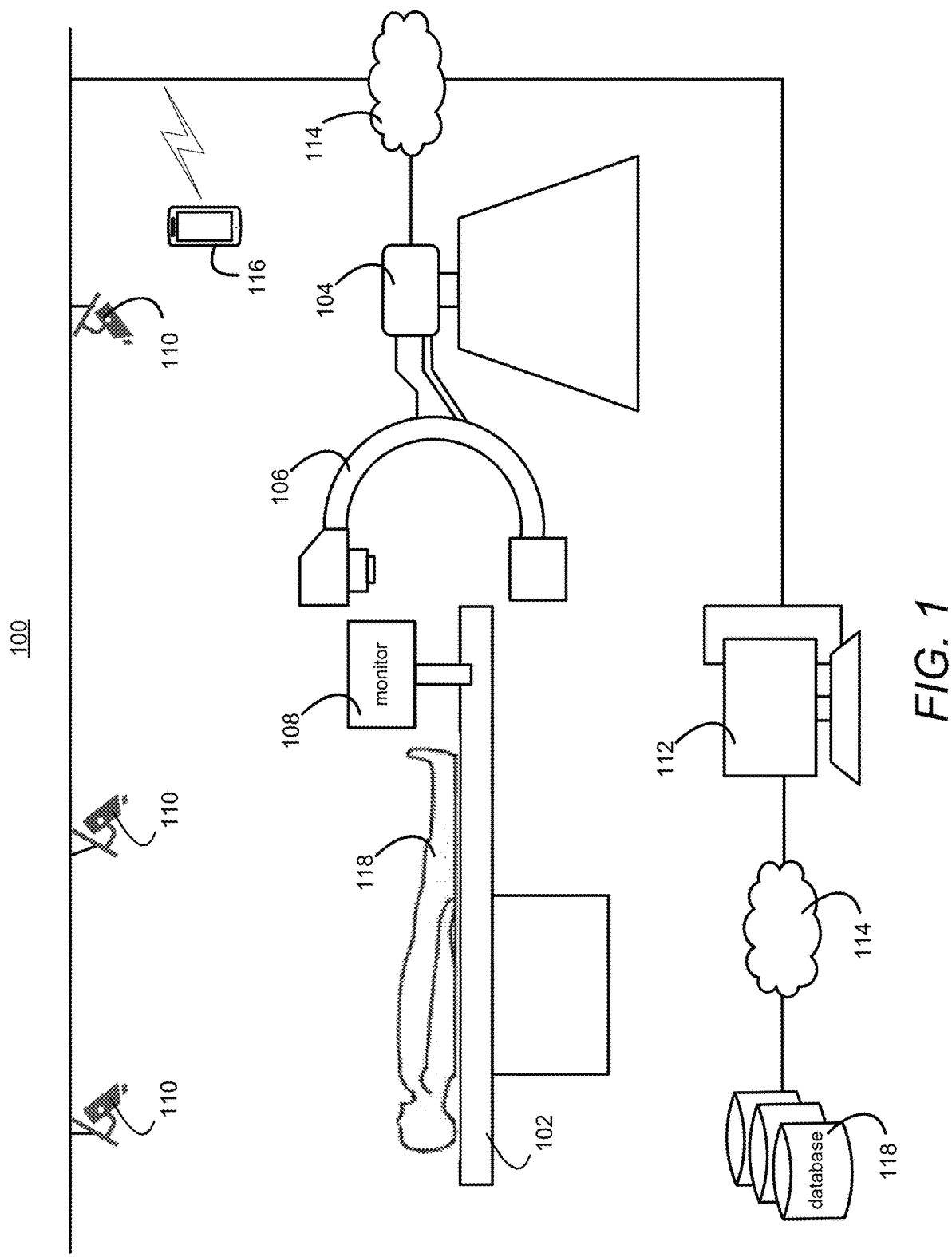
FIG. 1 is a block diagram illustrating an example system described herein that may be used to automate a medical environment.

FIG. 1 is a diagram illustrating a medical environment 100 that may be automated using systems, methods, and/or instrumentalities disclosed herein. The medical environment 100 may be any facility in a healthcare setting including, e.g., an operating room or a scan room at a hospital, a rehabilitation facility, a fitness center, etc. The medical environment 100 may be equipped with various tools, devices, and/or equipment such as a patient bed 102, an X-ray scanner 104 with a c-shaped arm (e.g., a C-arm 106), a patient monitoring device 108, etc. The tools, devices, and/or equipment may be maneuvered (e.g., manually or automatically) to accommodate the needs of a medical procedure being performed in the medical environment 100. For example, the patient bed 102 may be raised or lowered, the C-arm 106 of the X-ray scanner may be manipulated (e.g., moved, tilted, or rotated) towards a specific scan location, a lighting device (not shown) may be adjusted to focus on a surgical site, etc.

Part or all the operations in the medical environment 100 may be automated, for example, utilizing one or more sensing devices 110 and/or a processing device 112 (e.g., a processing device) communicatively coupled to the one or more sensing devices 110. The sensing devices 110 may be installed at various locations of the medical environment 100 and may be communicatively coupled to the processing device 112 and/or other devices of the medical environment 100 via a communication network 114. Each of the sensing devices 110 may include one or more sensors such as one or more 2D visual sensors (e.g., 2D cameras), one or more 3D visual sensors (e.g., 3D cameras), one or more red, green and blue (RGB) sensors, one or more depth sensors, one or more RGB plus depth (RGB-D) sensors, one or more thermal sensors (e.g., infrared (FIR) or near-infrared (NIR) sensors), one or more motion sensors, one or more radar sensors, and/or other types of image capturing circuitry that are configured to capture images of a person, an object or a scene in the medical environment 100. Depending on the type of cameras, sensors, and/or image capturing circuitry included in the sensing devices 110, the images generated by the sensing devices 110 may include, for example, one or more photos, one or more thermal images, one or more radar images, and/or the like. The sensing devices 110 may be configured to generate the images described herein in response to detecting a person, object, or scene in the medical environment 100. The sensing devices 110 may also be configured to generate the images described herein based on a preconfigured schedule or time interval, or upon receiving a control signal (e.g., from a remote device) that triggers the image generation.

Each of the sensing devices 110 may include a functional unit (e.g., a processor) configured to control the image capturing functionalities described herein. The functional unit may also be configured to process the images (e.g., pre-process the images before sending the images to another device), communicate with other devices located inside or outside of the medical environment 100, determine a characteristic of the medical environment 100 based on the captured images, etc. Each of the sensing devices 110 may include a communication circuit and may be configured to exchange information with one or more other sensing devices via the communication circuit and/or the communication network 114. The sensing devices 110 may form a sensor network within which the sensing devices may transmit data to and receive data from each other. The data exchanged between the sensing devices 110 may include, for example, imagery data captured by each sensing device and/or control data for discovering each sensing device's presence and/or calibrating each sensing device's parameters. For instance, when a new sensing device is added to the medical environment 100, the sensing device may transmit messages (e.g., via broadcast, groupcast or unicast) to one or more other sensing devices in the sensor network and/or a controller (e.g., a processing device as described herein) of the sensor network to announce the addition of the new sensing device. Responsive to such an announcement or transmission of data, the other sensing devices and/or the controller may register the new sensing device and begin exchanging data with the new sensing device.

The sensing devices 110 may be configured to be installed at various locations of the medical environment 100 including, e.g., on a ceiling, above a doorway, on a wall, on a medical device, etc. From these locations, each of the sensing devices 110 may capture images of a patient, object or scene that is in the field of view (FOV) of the sensing device (e.g., the FOV may be defined by a viewpoint and/or a viewing angle). The FOV of each of the sensing devices 110 may be adjusted manually or automatically (e.g., by transmitting a control signal to the sensing device) so that the sensing device may take images of a person, an object, or a scene in the medical environment 100 from different viewpoints or different viewing angles.

Each of the sensing devices 110 may be configured to exchange information with other devices in the medical environment 100, e.g., via the communication network 114. In examples, each of the sensing devices 110 may be configured to transmit the images captured by the sensing device to the processing device 112. In examples, the processing device 112 may be configured to retrieve the images captured by the sensing devices 110 from the sensing devices, e.g., via a pull mechanism. The transmission and/or retrieval of images may be performed on a periodic basis or in response to receiving a control signal instructing the transmission or retrieval. For instance, the processing device 112 may be configured to receive a notification from the sensing devices 110 when images are captured and retrieve the image in response to receiving the notification.

The configuration and/or operation of the sensing devices 110 may be at least partially controlled by a programming device 116. For example, the programming device 116 may be configured to initialize and modify one or more operating parameters of the sensing devices 110 including, e.g., the resolution of images captured by the sensing devices 110, a periodicity of data exchange between the sensing devices 110 and the processing device 112, a frame or bit rate associated with the data exchange, a duration of data storage on the sensing devices, etc. The programming device 116 may also be configured to control one or more aspects of the operation of the sensing devices 110 such as triggering a calibration of the sensing devices, adjusting the respective orientations of the sensing devices, zooming in or zooming out on a person or object in the medical environment 100, triggering a reset, etc. The programming device 116 may be a mobile device (e.g., such a smartphone, a tablet, or a wearable device), a desktop computer, a laptop computer, etc., and may be configured to communicate with the sensing devices 110 and/or the processing device 110 over the communication network 114. The programming device 116 may receive information and/or instructions from a user (e.g., via a user interface implemented on the programming device 116) and forward the received information and/or instructions to the sensing devices 110 via the communication network 114.

The communication network 114 described herein may be a wired or a wireless network, or a combination thereof. For example, the communication network 114 may be established over a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) or 5G network), a frame relay network, a virtual private network (VPN), a satellite network, and/or a telephone network. The communication network 114 may include one or more network access points. For example, the communication network 114 may include wired and/or wireless network access points such as base stations and/or internet exchange points through which one or more devices in the medical environment 100 may be connected to exchange data and/or other information. Such exchange may utilize routers, hubs, switches, server computers, and/or any combination thereof.

The processing device 112 may be configured to receive images from the sensing devices 110 and determine one or more characteristics of the medical environment 100 based on the images. These characteristics may include, for example, people and/or objects that are present in the medical environment 100 and respective locations of the people and/or objects in the medical environment 100. The people presented in the medical environment 100 may include, e.g., a patient 118 and/or medical staff (e.g., a physician, a technician, a nurse, etc.) attending to the patient 118. The objects presented in the medical environment 100 may include, e.g., the X-ray scanner 104, the C-arm 106, the monitoring device 108, the patient bed 102, and/or other devices or tools not shown in FIG. 1. Based on the determined characteristics of the medical environment 100, the processing device 112 may generate information (e.g., commands) for automating one or more aspects of the operations inside the medical environment 100. For example, in response to detecting the patient 118 and determining the respective locations of the patient 118 and the various devices in the medical environment 100, the processing device 112 may generate one or more messages (e.g., one or more instructions and/or commands) to maneuver at least a part of a target medical device (e.g., such as the C-arm 106 of the X-ray scanner 104 or a surgical robot) towards the patient 118, e.g., without requiring a physician or a technician to manually manipulate the target medical device. The location of the patient 118 may include a 3D location (e.g., in terms of [X, Y, Z] coordinates) of a scan or surgical site of the patient 118, and the processing device 112 may be configured to transmit the one or more control messages to the target medical device (e.g., a control unit of the target medical device) via a communications interface such as an application programming interface (API) to the target medical device. The communication interface may be implemented based on various protocols including, e.g., a representational state transfer (REST) protocol. The processing device 112 may determine potential obstacles (e.g., other tools or devices in the medical environment 100) between the patient 118 and the target medical device and include navigation instructions (e.g., navigation directions and/or step sizes) in the one or more messages generated by the processing unit 112 to prevent the target medical device from colliding with other objects (e.g., such as the monitoring device 108 shown in FIG. 1) and/or people (e.g., a physician attending to the patient 118) in the medical environment 100 while the medical device moves towards the patient 118.

The processing device 112 may be configured to transmit the one or more messages to a receiving device to control the target medical device based on the one or more messages. The receiving device may be the X-ray scanner 104 or a control unit of the X-ray scanner 104 that may be located inside the X-ray scanner 104 or remotely from the X-ray scanner 104 (e.g., in a separate room). The receiving device may be communicatively coupled to the processing device 112, for example, via the communication network 114. The processing device 112 may provide a notification to the receiving device and/or the medical staff attending to the patient 118 regarding the control operation(s) to be performed for the target medical device. For instance, the processing device 112 may estimate a movement path of the C-arm 106 towards the patient 118 based on the determined characteristics of the medical environment 100 (e.g., based on respective locations of the people and/or objects detected in the medical environment), and provide (e.g., indicate) the estimate to the receiving device and/or the medical staff. The estimate may be provided in various forms including, for example, a plot of the movement path or a simulation (e.g., an animated simulation) of the medical device's movements. The estimate may be presented on the monitoring device 108 or another suitable display device such as a display device attached to the processing device 112. The processing device 112 may also be configured to provide a visual representation of the layout of the medical environment 100 based on people and/or objects detected in the images captured by the sensing devices 110. The visual representation may indicate, for example, the people and/or objects detected in the medical environment 100 and/or their respective locations in the medical environment 100. The visual representation may be provided to the receiving device described herein and/or a controller of the medical environment 100 (e.g., a physician or technician supervising the medical environment 100).

Other aspects of the operations and/or workflows in the medical environment 100 may also be automated based on the images captured by the sensing devices 110. In examples, the processing device 112 may determine, based on one or more images of the patient 118, a human model (e.g., a 3D parametric human model) that reflects the shape, pose and/or motion of the patient 118. The processing device 112 may use such a human model to determine a scan or surgical area of the patient and generate instructions or commands to move a medical device (e.g., a scanner, a surgical robot, etc.) towards the determined scan or surgical area. The processing unit 112 may also adjust the parameters of a medical device (e.g., scan directions, radiation dosage, incision angels, etc.) to better target the scan or surgical area. Alternatively, or in addition, the processing device 112 may indicate the scan or surgical area to a physician (e.g., by highlighting the scan or surgical area on the human model) so that a scan or incision may be performed with improved accuracy. The processing device 112 may render a visualization (e.g., an augmented or virtual reality visualization) in which the 3D human model of the patient described herein may be overlaid with the 3D location of an organ or lesion of interest to provide real-time guidance (e.g., the human model and/or 3D location may be adjusted in real time based on the patient's position and/or pose) to a physician or technician during a medical procedure. The processing device 112 may also facilitate image registration (e.g., coarse-to-fine image registration) by fusing the images and/or visions captured by the sensing device 110. Examples of creating a human model for a patient based on one or more images of the patient can be found in commonly assigned U.S. patent application Ser. No. 16/860,901, filed Apr. 28, 2020, entitled "Sensing Device for Medical Facilities," the disclosure of which is hereby incorporated by reference in its entirety.

In examples, the processing device 112 may detect a radiation source in the images captured by the sensing devices 110 and further determine, based on the images, a location and/or orientation of the radiation source in the medical environment 100 relative to a person (e.g., the patient 118, a physician, a technician, etc.) in the medical environment 100. Responsive to the detection and/or determination, the processing device 112 may estimate a radiation exposure of the person (e.g., accumulated radiation over a time period) and provide notifications about the radiation exposure to the person (e.g., to alert the person about the exposure). The processing device 112 may acquire information about the operating parameters of the radiation source and generate the estimation based on these operating parameters. For example, the operating parameters may indicate the radiation intensity and/or radiation range of the radiation source (e.g., the parameters may reflect a radiation model of the radiation source). As such, based on the location and/or orientation of the radiation source indicated by the images, the processing device 112 may determine the amount of radiation that may reach the location of a person in the medical environment 100. The processing device 112 may further utilize a human mesh model of the person that may be derived from an image of the person to compute a radiation exposure value for a specific body part of the person (e.g., head, chest, etc.). The processing unit may provide the notifications about the radiation exposure in various forms including, e.g., a graph that depicts the radiation exposure of the person along a time axis. The processing device 112 may automatically adjust one or more parameters of the radiation source (e.g., directions and/or radiation intensity) based on the estimated radiation exposure of the person and/or a treatment or safety protocol concerning the person.

In examples, the processing device 112 may determine, based on the people, objects, and/or activities detected in the medical environment 100, the progression of a medical procedure for the patient 118. For instance, each phase of the medical procedure may be associated with a visual pattern such as certain personnel (e.g., an anesthesiologist) being in the medical environment 100, certain tools, devices, and/or medicines being deployed and/or administered, certain positions being taken by the patient 118, etc. The processing device 112 may acquire information about the visual patterns associated with various phases of the medical procedure, detect a specific pattern based on the images captured by the sensing devices 110, and determine a current phase of the medical procedure accordingly. The processing device 112 may optimize or provide recommendation for optimizing the workflow of the medical environment 100 based on the current and/or subsequent phases of the medical procedure. For instance, the processing device 112 may recommend, locate, and/or prepare tools or devices that may be needed for the current or subsequent phases of the medical procedure, the processing device 112 may detect anomalies in the medical environment 100 (e.g., identify redundant personnel in the medical environment), and/or the processing device 112 may conduct a time analysis of the medical procedure, for example, to determine whether the medical procedure is ahead or behind schedule.

In examples, the processing device 112 may be communicatively coupled to a database 120, for example, via the communication network 114. The database 120 may comprise a patient record repository that stores basic information of the patient 118, diagnostic and/or treatment histories of the patient 118, scan images of the patient 118, etc. As a part of the automation of a medical procedure for the patient 118, the processing device 112 may be configured to retrieve all or a subset of the medical records of the patient 118 from the database 120, analyze the retrieved medical records in conjunction with other information of the patient 118 gathered or determined by the processing device 112 (e.g., such as the human model described herein), and generate commands and/or information that enables one or more aspects of the medical procedure to be performed for the patient 118 without human invention. For example, based on past medical scans of the patient 118, body geometry of the patient 118, and/or other preferences and/or constraints associated with the patient 118, the processing device 112 may automatically determine the parameters and/or configurations of a device (e.g., the position and/or orientation of the C-arm 106) involved in the medical device and cause the parameters and/or configurations to be implemented for the device, e.g., by transmitting the parameters and/or configurations to a control unit of the device.

To determine the location of a person or object in the medical environment 100 based on images of the person or object captured by a sensing device, the spatial relationship between a coordinate system associated with the medical environment 100 (e.g., which may be referred to herein as a world coordinate system or a global coordinate system) and a coordinate system associated with the images (e.g., which may be referred to herein as an image coordinate system or a local coordinate system) may be established. For ease of description, it is assumed herein that the coordinate systems are Cartesian coordinate systems in which the location of a person or object may be defined using respective coordinates of the person or object in X, Y, or Z direction relative to an origin of the coordinate system. A skilled person in the art will understand, however, that other types of coordinate systems (e.g., such as a cylindrical coordinate system or a spherical coordinate system) may also be used without affecting the functionalities described herein.

Figure 2B:
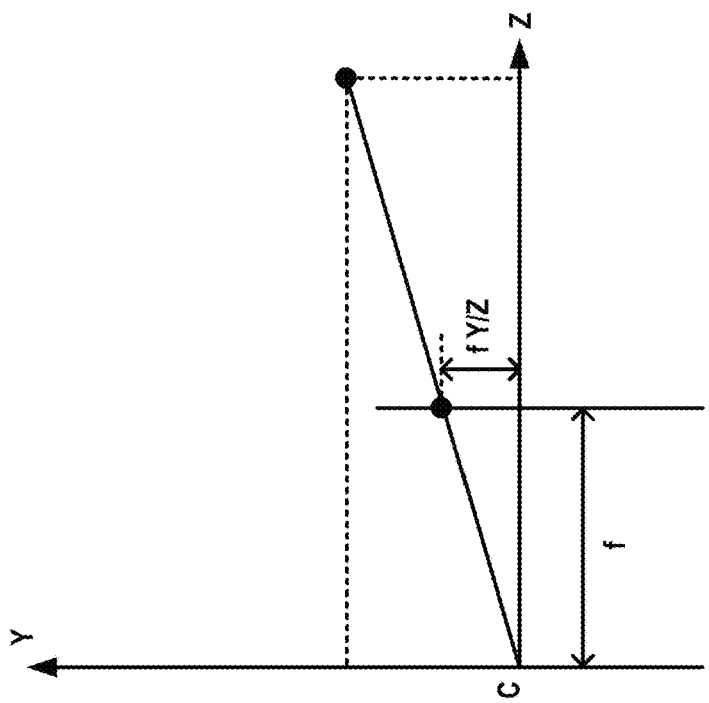
FIG. 2A and FIG. 2B are diagrams illustrating example geometry associated with camera projection.
Figure 2A:
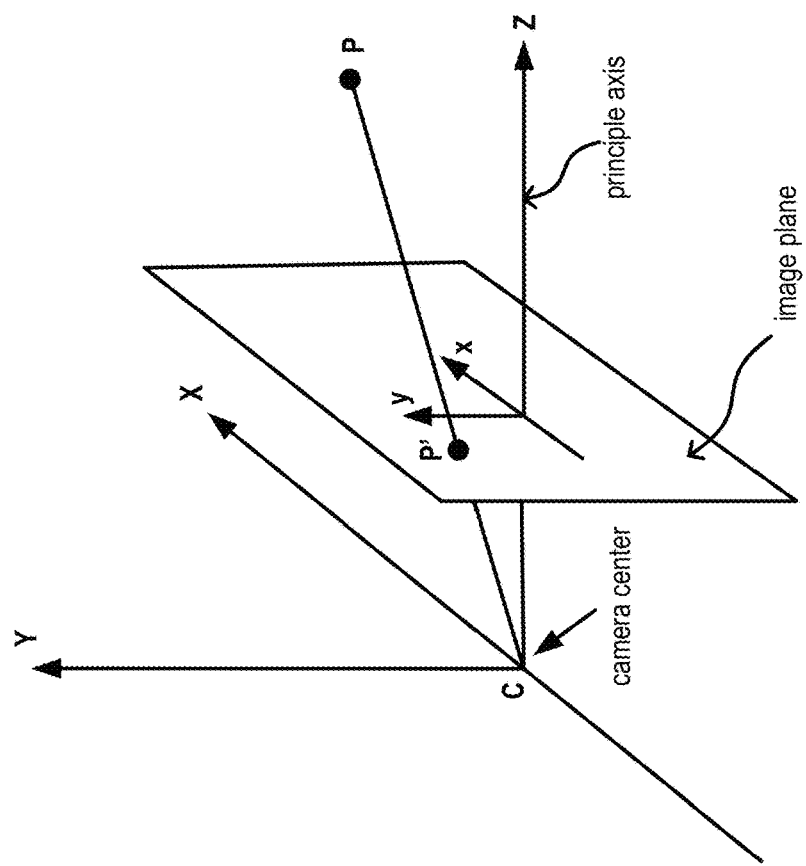

FIGS. 2A and 2B show example geometry associated with camera projection. As shown, a 3D point P in the world (e.g., in the medical environment 100 of FIG. 1) may be projected onto an image plane and become P'. Thus, given coordinates (X, Y, Z) of P in the world, the coordinates (x, y) of P' in the image plane can be derived as x=f X/Z and y=f Y/Z, where f may represent a focus length (e.g., a distance between the camera center and the projection plane) of the camera. Using homogeneous coordinates, the camera projection may be modeled as follows:

$$\begin{pmatrix} x \\ y \\ 1 \end{pmatrix} \sim \begin{pmatrix} f & 0 & 0 & 0 \\ 0 & f & 0 & 0 \\ 0 & 0 & 1 & 0 \end{pmatrix} \begin{pmatrix} X \\ Y \\ Z \\ 1 \end{pmatrix} \quad 1)$$

To express the distances in the model above with pixel coordinates and add a control over how pixels may be scaled in the x and y directions, the model shown above may be rewritten as:

$$\begin{pmatrix} x \\ y \\ 1 \end{pmatrix} \sim \begin{pmatrix} f_x & 0 & u_0 & 0 \\ 0 & f_y & v_0 & 0 \\ 0 & 0 & 1 & 0 \end{pmatrix} \begin{pmatrix} X \\ Y \\ Z \\ 1 \end{pmatrix} \quad 2)$$

where $f_x=s_x f$, $f_y=s_y f$, $s_x$ and $s_y$ may represent scaling factors in the x, y directions, and ($u_0$, $v_0$) may represent the pixel coordinates of the camera center in the image plane (e.g., the principle point).

A skew factor $\alpha$ may also be added to the model to account for the potential misalignment from a square pixel if the image plane axes are not precisely perpendicular. An internal camera model may then be expressed as:

$$\begin{pmatrix} x \\ y \\ 1 \end{pmatrix} \sim \begin{pmatrix} f_x & \alpha & u_0 & 0 \\ 0 & f_y & v_0 & 0 \\ 0 & 0 & 1 & 0 \end{pmatrix} \begin{pmatrix} X \\ Y \\ Z \\ 1 \end{pmatrix} \quad 3)$$

Furthermore, since the image coordinate system may be rotated and/or translated from the world coordinate system (e.g., via rigid transformation), the transformation of coordinates between the world coordinate system and the image coordinate system may further consider the rotation and/or translation between the two coordinate systems, as illustrated below:

$$\begin{pmatrix} x \\ y \\ 1 \end{pmatrix} \sim K[Rt] \begin{pmatrix} X \\ Y \\ Z \\ 1 \end{pmatrix} \quad 4)$$

where K (as shown below) may represent an intrinsic camera matrix that includes intrinsic parameters of the camera such as a focal length of the camera, pixel coordinates of the principle point, one or more scaling factors, a skew factor, etc., and [R t] (as shown below) may represent an extrinsic matrix that indicates the rotation and translation between the world coordinate system and the image coordinate system.

$$K = \begin{pmatrix} f_x & \alpha & u_0 \\ 0 & f_y & v_0 \\ 0 & 0 & 1 \end{pmatrix} \quad 5)$$

$$[Rt] = \begin{pmatrix} r_{11} & r_{12} & r_{13} & t_1 \\ r_{21} & r_{22} & r_{23} & t_2 \\ r_{31} & r_{32} & r_{33} & t_3 \end{pmatrix} \quad 6)$$

where the parameters r in the external matrix may represent respective rotation angles between corresponding axes of the world coordinate system and the image coordinate system, and where the parameters t in the external matrix may represent respective coordinate offsets between the origins of the world coordinate system and the image coordinate system.

For each sensing device, the parameters of the intrinsic and extrinsic matrices described herein may be determined by via one or more calibration operations. The calibration operations may be performed during or after the installation of the sensing device in the medical environment (e.g., after adding the sensing device to the sensor network described herein). The calibration may be performed autonomously without human intervention (e.g., utilizing preexisting markers and/or images taken by the sensing device). For example, the intrinsic and extrinsic parameters may be estimated utilizing a homography matrix H that represents a transformation between an image projection plane and an image (e.g., between a point M on the image projection plane and a corresponding point m in the image). Such transformation may be expressed as follows:

$$\begin{pmatrix} x \\ y \\ 1 \end{pmatrix} \sim \begin{pmatrix} h_{11} & h_{12} & h_{13} \\ h_{21} & h_{22} & h_{23} \\ h_{31} & h_{32} & h_{33} \end{pmatrix} \begin{pmatrix} X \\ Y \\ 1 \end{pmatrix} \quad 7)$$

where (x, y, 1) and (X, Y, 1) may represent the coordinates of the points M and m, respectively.

Based on 4)-6) and assuming, without loss of generality, that the image projection plane of the sensing device is on Z=0 of the world coordinate system, the following may also be obtained:

$$\begin{pmatrix} x \\ y \\ 1 \end{pmatrix} \sim \begin{pmatrix} f_x & \alpha & u_0 \\ 0 & f_y & v_0 \\ 0 & 0 & 1 \end{pmatrix} \begin{pmatrix} r_{11} & r_{12} & t_1 \\ r_{21} & r_{22} & t_2 \\ r_{31} & r_{32} & t_3 \end{pmatrix} \begin{pmatrix} X \\ Y \\ 1 \end{pmatrix} \quad 8)$$

(e.g., by making Z=0 and deleting the third column from 6)). From 7) and 8), the following equation may be derived:

$$\begin{pmatrix} f_x & \alpha & u_0 \\ 0 & f_y & v_0 \\ 0 & 0 & 1 \end{pmatrix} \begin{pmatrix} r_{11} & r_{12} & t_1 \\ r_{21} & r_{22} & t_2 \\ r_{31} & r_{32} & t_3 \end{pmatrix} = \begin{pmatrix} h_{11} & h_{12} & h_{13} \\ h_{21} & h_{22} & h_{23} \\ h_{31} & h_{32} & h_{33} \end{pmatrix}, \quad 9)$$

which may be expressed as $K(r_1, r_2, t) = (h_1, h_2, h_3)$. Based on 9), the following may be further obtained:

$$h_1^T K^{-T} K^{-1} h_2 = 0 \quad (10)$$

$$h_1^T K^{-T} K^{-1} h_1 - h_2^T K^{-T} K^{-1} h_2 = 0 \quad (11)$$

Now let $$B = K^{-T} K^{-1} = \begin{pmatrix} B_{11} & B_{12} & B_{13} \\ B_{21} & B_{22} & B_{23} \\ B_{31} & B_{32} & B_{33} \end{pmatrix}.$$

may be symmetric and may be defined by a vector $b=(B_{11}, B_{12}, B_{13}, B_{22}, B_{23}, B_{33})^T$. By denoting the $i^{th}$ column of the homography matrix $H$ as $h_i=(h_{i1}, h_{i2}, h_{i3})^T$, the following may be derived:

$$h_i^T B h_j = v_{ij}^T b \quad (12)$$

where $v_{ij}=(h_{i1}h_{j1}, h_{i1}h_{j2}+h_{i2}h_{j1}, h_{i2}h_{j2}, h_{i3}h_{j1}+h_{i1}h_{j3}, h_{i3}h_{j2}+h_{i2}h_{j3}, h_{i3}h_{j3})^T$. Given a homography matrix $H$, the constraints of 10) and 11) can then be rewritten as homogeneous equations in b:

$$\begin{pmatrix} v_{12}^T \\ (v_{12} - v_{12})^T \end{pmatrix} b = 0 \quad (13)$$

Thus, based on n images of the image projection plane, n equations like 13) may be stacked together to obtain the following:

$$Vb = 0 \quad (14)$$

where $V$ may be a 2n×6 matrix.

Since B has 6 degrees of freedom and the homography matrix H has 8 degrees of freedom, b may be uniquely solved (e.g. up to a scaling factor) using three or more images of a plane (e.g., such as the image projection plane) and four or more points associated with the plane (e.g., since each of the points on the plane and a corresponding point in an image taken thereof may provide two equations). And once b is estimated, the intrinsic matrix K of the sensing device may be determined, for example, as follows:

$$v_0 = (B_{12}B_{13} - B_{11}B_{23})/(B_{11}B_{22} - B_{12}^2)$$

$$\lambda = B_{33} - [B_{13}^2 + v_0(B_{12}B_{13} - B_{11}B_{23})]/B_{11}$$

$$f_x = \sqrt[2]{\lambda/B_{11}}$$

$$f_y = \sqrt[2]{\lambda B_{11}/(B_{11}B_{22} - B_{12}^2)}$$

$$\alpha = -B_{12}f_x^2 f_y/\lambda$$

$$u_0 = \alpha v_0/f_y - B_{13}\alpha^2/\lambda$$

where $\lambda$ may represent a scaling factor (e.g., an arbitrary scaling factor).

Using the determined K, the extrinsic parameters associated with the sensing device may be derived, for example, based on the following:

$$r_1 = \lambda K^{-1} h_1$$

$$r_2 = \lambda K^{-1} h_2$$

$$r_3 = r_1 \times r_2$$

$$t = \lambda K^{-1} h_3$$

where $\lambda = 1/\|K^{-1}h_1\| = 1/\|K^{-1}h_2\|$.

Figure 3:
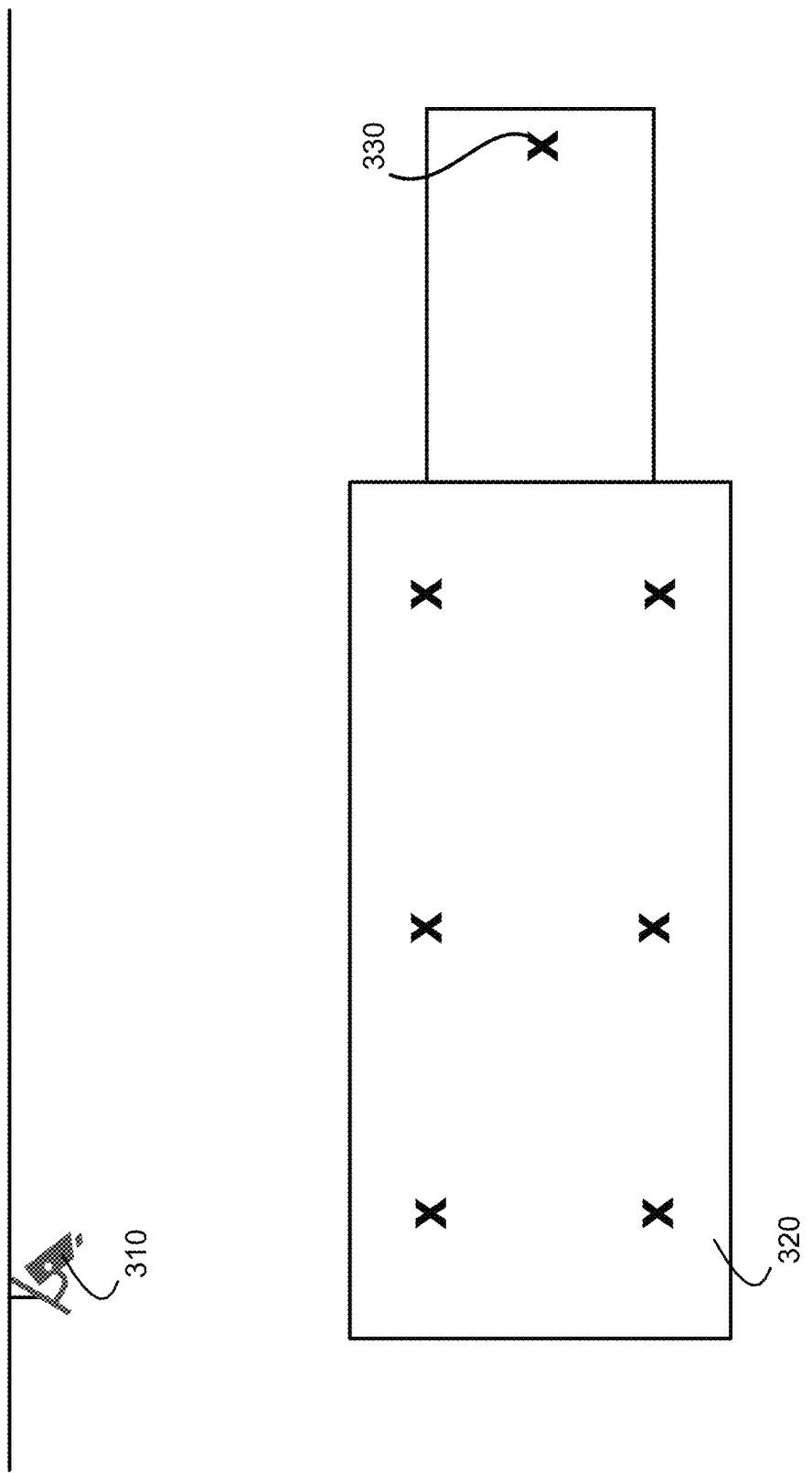
FIG. 3 is a diagram illustrating an example of calibrating a sensing device described herein.

Various techniques may be utilized during the calibration of a sensing device to obtain the images (e.g., of a plane) and feature points (e.g., in the plane) needed for estimating the intrinsic and extrinsic parameters described herein. FIG. 3 shows an example of calibrating a sensing device 310. As shown, a planar surface 320 may be identified in the medical environment in which the sensing device 310 is installed. Such a planar surface 320 may be, for example, a patient bed located in a scan or operating room. The planar surface 320 may comprise multiple markers 330 (e.g., feature points such as the "X" shown in FIG. 3) that may be existing parts of the planar surface (e.g., marks engraved into the surface panel) and/or marks specifically created and placed on the planar surface 320 for purposes of calibrating the sensing device 310. As described herein, four or more markers associated with the planar surface 320 and three or more images of the planar surface 320 that comprise the markers may be used to uniquely determine the homography matrix H and/or the intrinsic and extrinsic parameters of the camera model associated with the sensing device 310. The position of the planar surface 320 may be manipulated (e.g., raised, lowered, and/or tilted) during the calibration to augment (e.g., artificially) the number of markers and/or images that may be used to perform the calibration. While the planar surface 320 is in a specific position, a set of images may be taken of the planar surface 320 using the sensing device 310 and the respective (x, y) coordinates of the markers in each of the captured images may be determined, for example, by the sensing device 310 or a processing device (e.g., such as the processing device 112 of FIG. 1) configured to facilitate the calibration of the sensing device 310. The (X, Y, Z) coordinates of each of the markers in the world coordinate system may be determined, for example, based on configuration information received by the sensing device 310 or the processing device, based on measurement obtained during an installation or set-up procedure, etc. The homography matrix H and/or the intrinsic and extrinsic parameters of the sensing device 310 may then be derived based on the camera and world coordinates of the markers in the captured images.

Once the intrinsic and extrinsic camera model parameters of a sensing device are determined, the location of a person or object in the world (e.g., the (X, Y, Z) coordinates of the person or object in the medical environment 100) may be derived based on the coordinates (e.g., in the image coordinate system) of the person or object in one or more images. For example, given the image coordinates (x,y) and a depth value z (e.g., which may be obtained from a depth image or based on multiple 2D images) of an object or person, the world coordinates P of the object or person may be determined as follows:

$$C = \text{inv}(K)*(x,y,1)*z \quad (15)$$

$$P = \text{inv}(R)*(C-t) \quad (16)$$

where K may represent the intrinsic matrix described herein, R may represent the rotation matrix described herein, and t may represent the translation vector described herein.

If the sensing device comprises a 3D visual sensor such as a depth or stereo camera, the Z coordinate of the person or object in the world coordinate system may be derived based on the depth information, D, provided by the 3D visual sensor. The (X, Y, Z) coordinates of the person or object in the world coordinate system may then be computed based on 15) and 16) by filling in the (x, y) coordinates of the person or object in an image and making Z=D. If the sensing device comprises a 2D visual sensor that may not provide depth information for the person or object, the Z coordinate of the person or object in the world coordinate system may be derived using images captured by multiple sensing devices and the 3D location of the person or object may then be computed based on 15) and 16), similar to the 3D sensor example.

Figure 4:
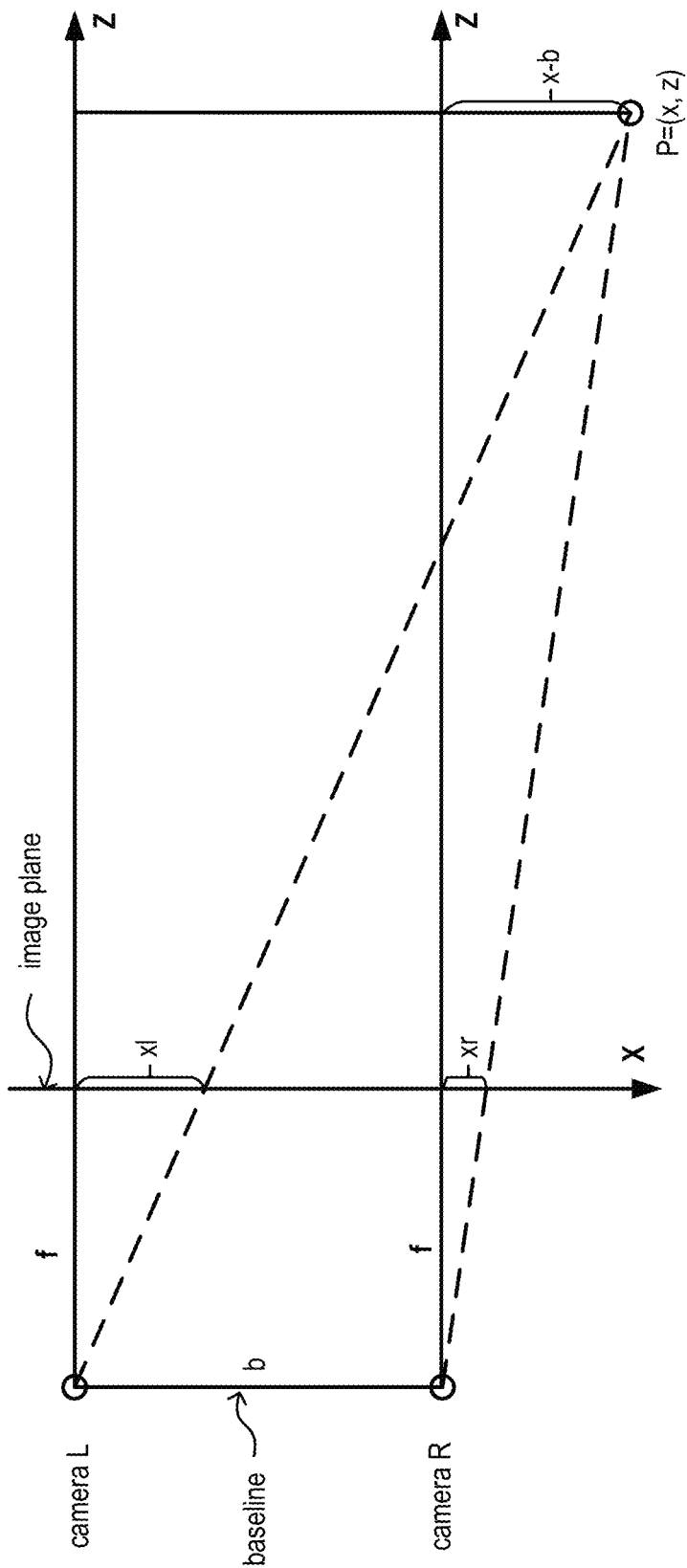
FIG. 4 is a diagram illustrating an example of depth determination based on images captured by two sensing devices describe herein.

FIG. 4 shows an example of determining the depth of a point P based on images captured by two cameras L and R (e.g., using triangulation). As shown, the point P may be projected onto respective image planes of the two cameras L and R. Based on the geometry shown in FIG. 5, the following may be established:

$$z/f = x/xl$$

$$z/f = (x-b)/xr$$

$$z/f = y/yl = y/yr$$

where f may represent the focal length of the cameras L and R that may be determined as a part of the intrinsic parameters described herein, (x, y, z) may represent the coordinates of point P (the Y-axis is perpendicular to the page), and xl, yl, xr, and xl may represent the projected coordinates of point P on the respective image planes of the cameras L and R. From the above, the depth (e.g., Z coordinate) of point P may be determined based on the disparity between the projected coordinates of point P on the respective image planes of the cameras L and R, e.g., as follows:

$$z = f*b/(xl-xr)$$

In example implementations, a processing device as described herein (e.g., the processing device 112 of FIG. 1) may be configured to receive images (e.g., 2D images) from multiple sensing devices and apply the techniques described herein to determine the depth location (e.g., Z coordinate) of a person or object included in the images. Using the depth information and the coordinates of the person or object in one or more of the images, the processing device may further determine the remaining coordinates (e.g., X and Y) of the person or object in the world coordinate system, e.g., based on 15) and 16). In examples, the area of an image that represents the person or object may be determined using the image recognition or segmentation techniques described herein, and the coordinates of the person or object in the image may be determined based on a center pixel of the image area that represents the person or object. In examples, the coordinates of the person or object in an image such as the coordinates of one or more keypoints of the person or object (e.g., nose, left hand, etc.) may be determined based on a human mesh model of the person or object estimated from the image (e.g., the human mesh model may be a parametric model that defines the locations of the keypoints).

A processing device as described herein (e.g., the processing device 112 of FIG. 1) may be configured with image recognition capabilities for identifying a person or object in an image captured by a sensing device (e.g., the sensing devices 110 of FIG. 1). The recognition of the person or object may serve multiple purposes including, for example, determining coordinates of the person or object in an image, tracking the person or object across multiple images, automatically retrieving medical records of the person from a repository (e.g., the database 118 of FIG. 1), etc.

The processing device may be configured to perform image recognition related functionalities via an artificial neural network such as a convolutional neural network (CNN). The CNN may be trained to receive an image, extract visual features or patterns from the image (e.g., in the form of a feature map or feature vector), and produce an output indicating whether the extracted features or patterns fall within a specific category or class (e.g., a patient, a physician, a specific medical device such as the C-arm 106 shown in FIG. 1, etc.). The CNN may include multiple layers including, e.g., an input layer, one or more convolutional layers, one or more pooling layers, one or more fully connected layers, and/or an output layer. Each of the convolutional layers may include a plurality of filters (e.g., kernels) configured to detect keypoints in an image that collectively represent a visual feature or pattern. The filters may be assigned respective weights that, when applied to an input, produce an output that indicates whether a certain feature or pattern is detected. The weights of the CNN may be learned through a training process. For example, during the training, the CNN may receive various training images and may process these images using currently assigned weights to make a prediction about whether a person or object (e.g., a medical device described herein) has been identified in an image. The prediction may be compared with a ground truth and a difference between the prediction and the ground truth may be determined, for example, based on a loss function. The CNN may then update its weights based on the determined loss (e.g., based on a gradient descent of the loss function) with an objective to reduce the difference between the prediction and the ground truth. The CNN may repeat these operations through multiple training iterations and/or for multiple training images until a set of predefined training termination criteria has been satisfied.

Figure 5:
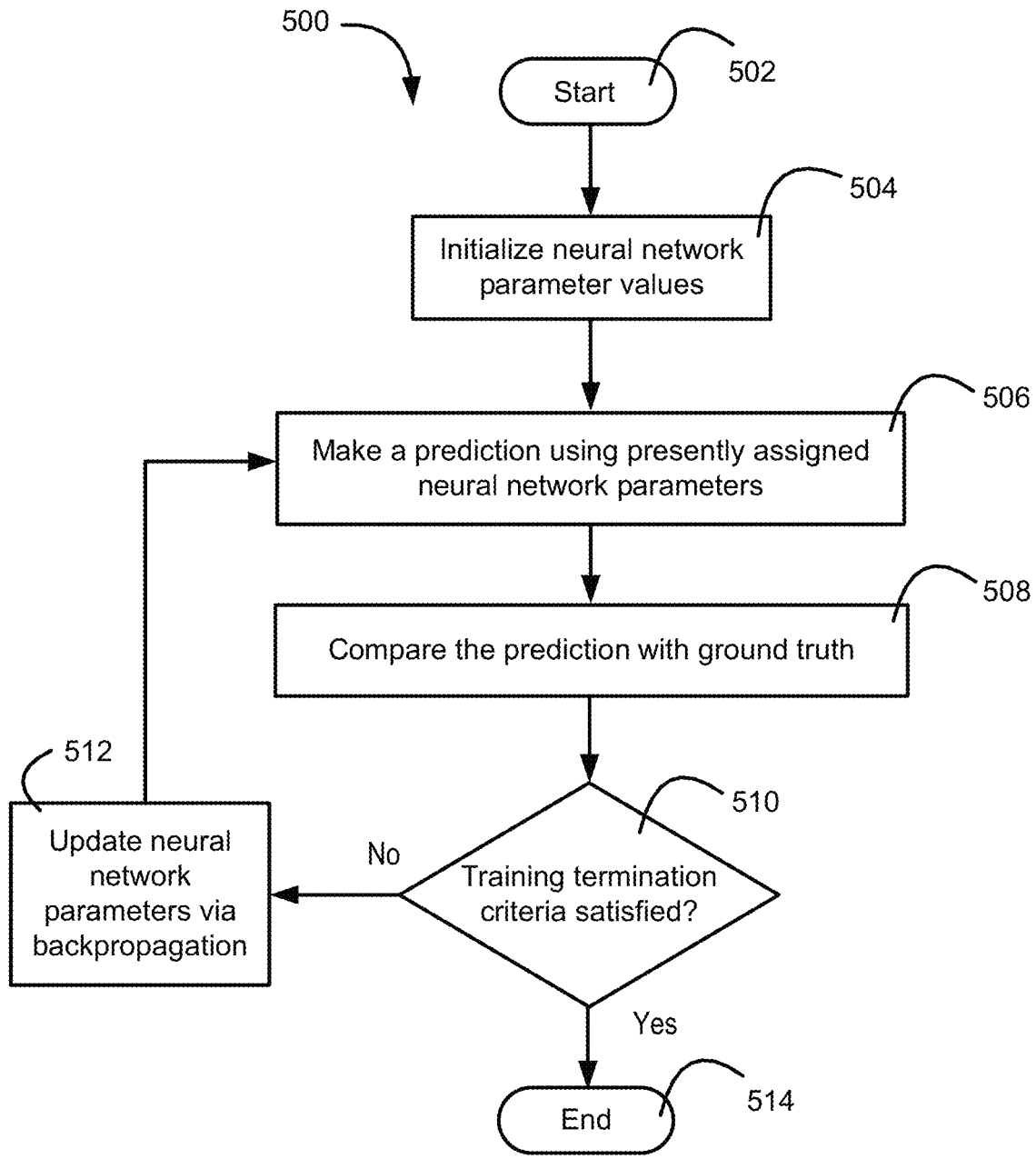
FIG. 5 is a flow diagram illustrating an example of training an artificial neural network to detect a person or an object in an image.

FIG. 5 illustrates an example process 500 for training a neural network described herein to perform image recognition. The process 500 may start at 502 and, at 504, the neural network may initialize its operating parameters such as the weights associated with one or more filters or kernels of the neural network. The neural network may initialize the parameters may be initialized, for example, based on samples from one or more probability distributions or parameter values of another neural network with a similar architecture. At 506, the neural network may receive a training image, process the image through various layers of the neural network, and make a prediction using presently assigned parameters of the neural network. The prediction may be, for example, whether the training image includes a person (e.g., a patient, a physician, etc.) and/or a specific object (e.g., a medical device such as the C-arm 106 shown in FIG. 1). At 508, the neural network may compare the prediction result with a ground truth and determine a difference between the prediction result and the ground truth, e.g., using a loss function. The loss function may be based on, for example, a mean squared error (MSE) between the prediction and the ground truth. At 510, the neural network may determine whether one or more training termination criteria are satisfied. For example, the neural network may determine that the training termination criteria are satisfied if the difference between the prediction result and the ground truth is below a predetermined threshold, if a change in the loss function between two training iterations is below a predetermined threshold, or if the neural network has completed a pre-determined number of training iterations. If the determination at 510 is that the training termination criteria are not satisfied, the neural network may proceed to 512 to update the presently assigned neural network parameters via backpropagation. The update may be performed, for example, based on a gradient descent (e.g., a stochastic gradient decent) associated with the loss function. The neural network may then return to 506 to repeat the operations of 506-510. If the determination at 510 is that the training termination criteria are satisfied, the neural network may end the training process 500 at 514.

In the examples provided herein, one or more of the tasks are described as being initiated and/or implemented by a processing device such as the processing device 112, for example, in a centralized manner. It should be noted, however, that the tasks may also be distributed among multiple processing devices (e.g., interconnected via the communication network 114, arranged in a cloud-computing environment, etc.) and performed in a distributed manner. Further, even though the processing device has been described herein as a device separate from the sensing devices (e.g., the sensing devices 110), the functionalities of the processing device may be realized via one or more of the sensing devices (e.g., the one or more sensing devices 110 may comprise respective processors configured to perform the functions of the processing device 112 described herein). So, in some example implementations, a separate processing device may not be included and one or more sensing devices (e.g., the sensing devices 110) may assume the responsibilities of the processing device.

Figure 6:
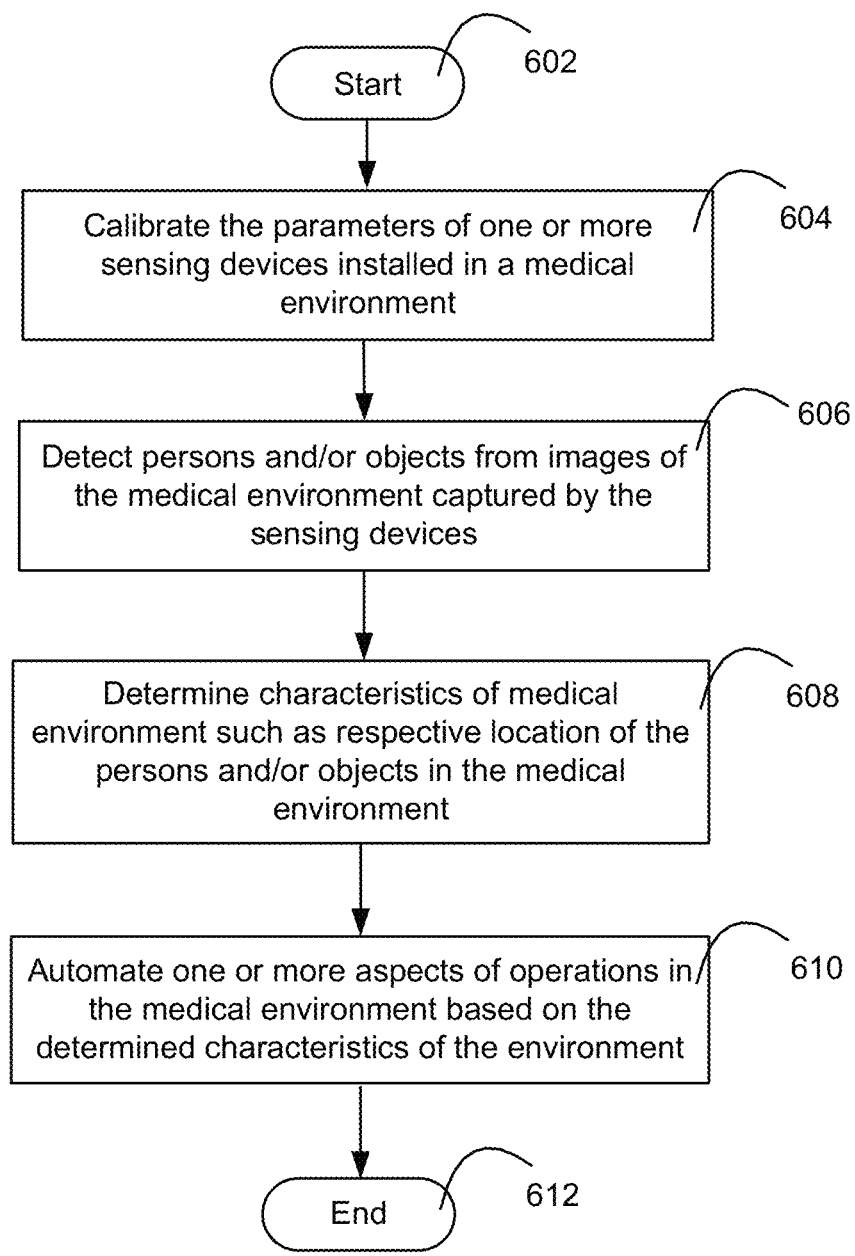
FIG. 6 a flow diagram illustrating example operations that may be performed during automation of a medical environment.

FIG. 6 shows example operations that may be performed by a processing device (e.g., the processing device 112 of FIG. 1) and/or one or more sensing devices (e.g., the sensing devices 110) to automate a medical environment (e.g., the medical environment 100 of FIG. 1). The operations may start at 602. At 604, the one or more sensing devices (e.g., which have been installed in the medical environment) may be calibrated in preparation for operating in the medical environment. The calibration may be performed by the processing device (e.g., using images captured by each sensing device) and/or by each sensing device (e.g., in communication with the processing device and/or one or more other sensing devices). For ease of description, at least some of the calibration operations will be described herein as being performed by the processing device even though they may also be performed by one or more sensing devices. The calibration may include determining respective parameters of the sensing devices that may include, for example, intrinsic and extrinsic parameters associated with respective visual sensors (e.g., cameras) of the sensing devices, as described herein. To determine these parameters, each sensing device may be configured to take one or more images of an object (e.g., a patient bed) in the medical environment. The object may comprise multiple markers (e.g., as shown in FIG. 3) and the images may be taken while the object is in different positions such as when the object is at different elevations (e.g. so as to increase the amount of data that may be used for the calibration). The images may be transmitted to the processing device, upon which the processing device may detect (e.g., automatically via a CNN) the markers in the images and further determine the coordinates of the markers (e.g., in the image coordinate system) in the images. The processing device may also acquire world coordinates of the markers (e.g., in the medical environment), for example, based on configuration information of the medical environment. The processing device may then determine the intrinsic and extrinsic camera parameters of the sensing device (and/or a homography matrix H associated with the sensing device) based on the camera and world coordinates of the markers in the captured images.

Once the sensing devices are calibrated, they may start capturing and/or transmitting images of the medical environment to the processing device at 606. Responsive to receiving the images, the processing device may, e.g., via a CNN of the processing device, analyze the images (e.g., at a pixel level), extract visual features from the images, and identify one or more persons (e.g., physicians and/or patients) and/or objects (e.g., tools, devices, etc.) in the images. At 608, the processing device may determine characteristics of the medical environment based on the persons and/or objects detected in the images and/or other information that may be acquired by the processing device. For instance, the processing device may determine respective locations of the persons or objects in the medical environment and learn a spatial relationship of the persons or objects based on the determined locations. The processing device may assemble information from multiple images (e.g., stitching the multiple images together) that may be captured by different sensing devices in order to determine the location of a person or object. The processing device may accomplish this task by utilizing knowledge about the parameters of the sensing devices (e.g., such as the relative positions of the sensing devices) that the processing device may have acquired via the calibration process described herein. For example, the processing device may determine the depth (e.g., a Z coordinate) of a person or object in the medical environment based on two images captured by respective sensing devices, e.g., using the triangulation technique described herein. The processing device may also determine the (X, Y) coordinates of the person or object in the medical environment based on the camera parameters of the sensing device and/or the (x, y) coordinates of the person or object in the image.

At 610, the processing device may generate information and/or control signals for automating one or more aspects of the operations in the medical environment. For example, the processing device may transmit a message to a receiving device (e.g., a control unit of a medical device such as the C-arm X-ray scanner described herein) so that a medical device may be moved automatically towards a patient in the medical environment. The message may include location information of the medical device and/or the patient in the medical environment, and/or navigation instructions for the medical device so that the medical device may not collide with other objects in the environment while moving towards the patient. As another example, the processing device may detect redundant personnel, tools, and/or devices in the medical environment and report the detection, for example, to a controller of the medical environment. As yet another example, the processing device may perform a time analysis of the operations being carried out in the medical environment and determine a current phase of a medical procedure being performed for a patient. The processing device may then automatically recommend and/or locate tools or devices to accommodate the current and/or subsequent phases of the medical procedure.

The processing device may continuously perform the operations of 604-610, for example, as new sensing devices are added and/or new objects and persons are detected in the medical environment. The processing device may cease performing these operations (e.g., entering an idle state) at 612, for example, if the processing device detects no activities in the medical environment and/or if the processing device receives a command to cease the operations.

Figure 7:
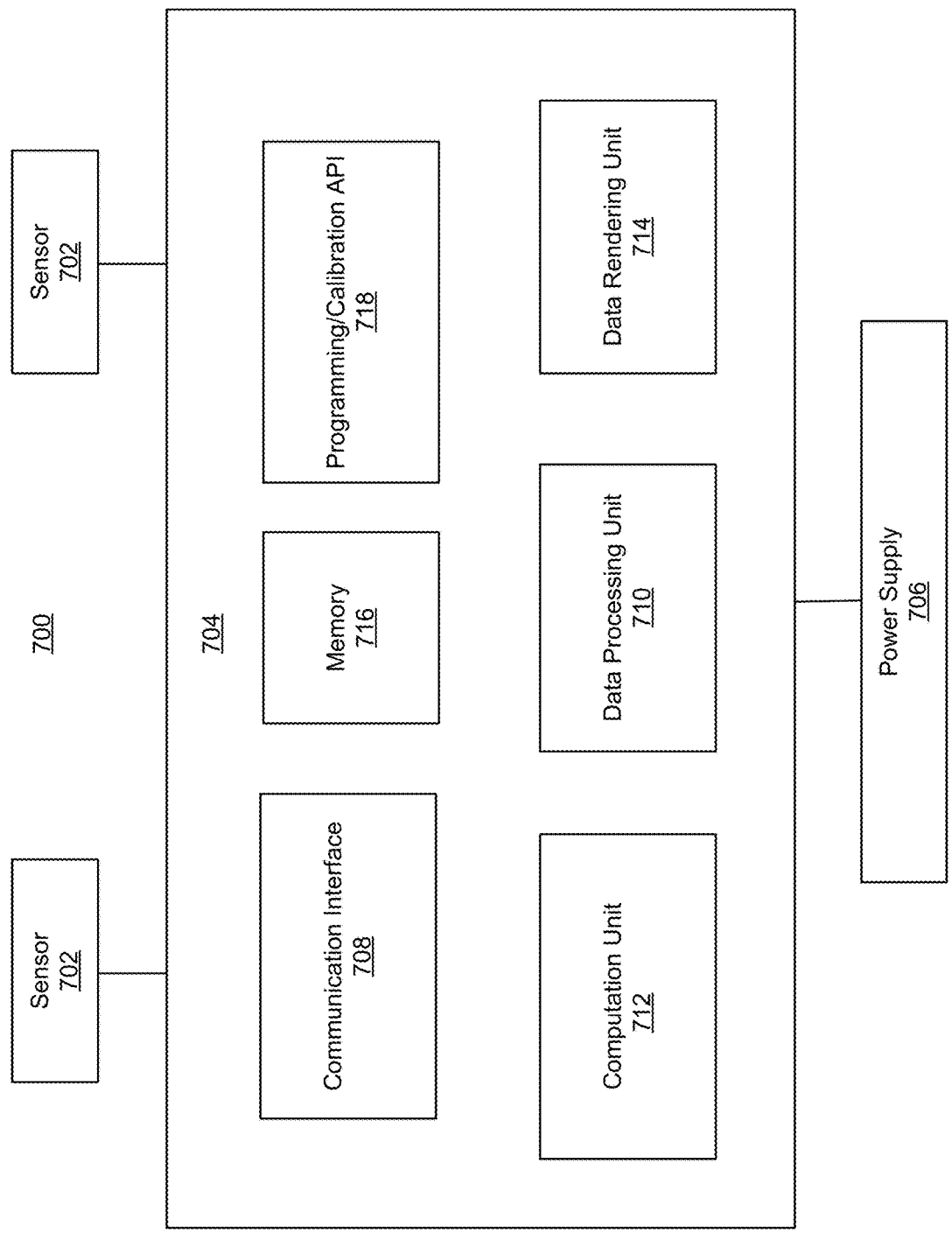
FIG. 7 a block diagram illustrating an example of a sensing device described herein.

FIG. 7 illustrates an example sensing device 700 (e.g., the sensing devices 110 shown in FIG. 1) that may be placed or installed in a medical environment (e.g., the medical environment 100 of FIG. 1) to facilitate automation of the medical environment. The sensing device 700 may comprise a sensor 702, a functional unit 704, and/or a power supply 706 that may be configured to be hosted in a housing. Although two sensors are shown in the figure, the sensing device 700 may comprise any number of sensors. Further, although one or more of the components are shown in FIG. 7 as being inside or outside of the functional unit 704, these components may be moved out of or into the functional unit 704 without affecting the functionalities of the sensing device described herein.

As described herein, the sensor 702 may include a RGB sensor, a depth sensor, a RGB plus depth (RGB-D) sensor, a thermo sensor such as a FIR or NIR sensor, a radar sensor, a motion sensor, a camera (e.g., a digital camera) and/or other types of image capturing circuitry configured to generate images (e.g., 2D images or photos) of a person, object, and/or scene in the FOV of the sensor. The images generated by the sensor 702 may include, for example, one or more photos, thermal images, and/or radar images of the person, object or scene. Each of the images may comprise a plurality of pixels that collectively represent a graphic view of the person, object or scene and that may be analyzed to extract features that are representative of one or more characteristics of the person, object or scene.

The sensor 702 may be communicatively coupled to the functional unit 704, for example, via a wired or wireless communication link. The sensor 702 may be configured to transmit images generated by the sensor to the functional unit 704 (e.g., via a push mechanism) or the functional unit 704 may be configured to retrieve images from the sensor 702 (e.g., via a pull mechanism). The transmission and/or retrieval may be performed on a periodic basis (e.g., based on a preconfigured schedule) or in response to receiving a control signal triggering the transmission or retrieval. The functional unit 704 may be configured to control the operation of the sensor 702. For example, the functional unit 704 may transmit a command to adjust the FOV of the sensor 702 (e.g., by manipulating a direction or orientation of the sensor 702). As another example, the functional unit 704 may transmit a command to change the resolution at which the sensor 702 takes images of a person, object or scene.

The sensor 702 and/or the functional unit 704 (e.g., one or more components of the functional unit 704) may be powered by the power supply 706, which may comprise an alternative current (AC) power source or a direct current (DC) power source (e.g., a battery power source). When a DC power source such as a battery power source is used, the power supply 706 may be rechargeable, for example, by receiving a charging current from an external source via a wired or wireless connection. For example, the charging current may be received by connecting the sensing device 700 to an AC outlet via a charging cable and/or a charging adaptor (including a USB adaptor). As another example, the charging current may be received wirelessly by placing the sensing device 700 into contact with a charging pad.

The functional unit 704 may comprise one or more of a communication interface circuit 708, a data processing device 710, a computation unit 712, a data rendering unit 714, a memory 716, or a programming and/or calibration application programming interface (API) 718. It should be noted that the components shown in FIG. 7 are provided merely as examples and are not meant to limit the scope of the disclosure. For example, the functional unit 704 is not restricted to including the exact components as shown in FIG. 7. Two or more of the components (e.g., functionalities of the components) may be combined, any one of the components may be divided into sub-components, any one of the components may be omitted, more components may be added, etc. As such, even though the functionalities of the sensing device 700 are described herein as being associated with respective one or more of the components, it will be appreciated that those functionalities may also be performed by a different component and/or be divided among multiple other components.

The functional unit 704 may be configured to receive or retrieve images from the sensor 702 via the communication interface circuit 708, which may include one or more wired and/or wireless network interface cards (NICs) such as ethernet cards, WiFi adaptors, mobile broadband devices (e.g., 4G/LTE/5G cards or chipsets), etc. In examples, a respective NIC may be designated to communicate with a respective sensor. In examples, a same NIC may be designated to communication with multiple sensors.

The images received or retrieved from the sensor 702 may be provided to the data processing device 710, which may be configured to analyze the images and carry out one or more of the operations described herein (e.g., including operations of the processing device 112 described herein). The functionality of the data processing device 710 may be facilitated by the computation unit 712, which may be configured to perform various computation intensive tasks such as feature extraction and/or feature classification based on the images produced by the sensor 702. The computation unit 712 may be configured to implement one or more neural networks such as the one or more CNNs described herein. The data rendering unit 714 may be configured to generate the one or more visual representations described herein including, e.g., a representation of a 2D or 3D human model, a simulation of the medical environment, etc.

Each of the data processing device 710, the computation unit 712, or the data rendering unit 714 may comprise one or more processors such as a central processing device (CPU), a graphics processing device (GPU), a microcontroller, a reduced instruction set computer (RISC) processor, an application specific integrated circuit (ASIC), an application-specific instruction-set processor (ASIP), a physics processing device (PPU), a digital signal processor (DSP), a field programmable gate array (FPGA), or a combination thereof. The data processing device 710, computation unit 712, and/or data rendering unit 714 may also comprise other type(s) of circuits or processors capable of executing the functions described herein. Further, the data processing device 710, the computation unit 712, or the data rendering unit 714 may utilize the memory 716 to facilitate one or more of the operations described herein. For example, the memory 716 may include a machine-readable medium configured to store data and/or instructions that, when executed, cause the processing device 710, the computation unit 712, or the data rendering unit 714 to perform one or more of the functions described herein. Examples of a machine-readable medium may include volatile or non-volatile memory including but not limited to semiconductor memory (e.g., electrically programmable read-only memory (EPROM), electrically erasable programmable read-only memory (EEPROM)), flash memory, and/or the like. And even though not shown in FIG. 7, the sensing device 700 may also comprise one or more mass storage devices that include a magnetic disk such as an internal hard disk, a removable disk, a magneto-optical disk, a CD-ROM or DVD-ROM disk, etc., on which instructions and/or data may be stored to facilitate the performance of the functions described herein.

The operation of the sensing device 700 may be configured and/or controlled through the programming/calibration API 718, for example, using a remote programming device such as the programming device 116 in FIG. 1. In examples, the programming/calibration API 718 may be configured to receive commands (e.g., one or more digital messages) from the programming device that adjust the operating parameters of the sensing device 700 such as the orientation and/or FOV of a sensor, a resolution at which a sensor captures images, a periodicity at which images are received or retrieved from a sensor, etc. In response to receiving a command from the programming device, the sensing device 700 (e.g., the functional unit 704) may adjust one or more aspects of its operation in accordance with the command. For instance, if the command specifies a higher output quality, the sensing device 700 may output a high-resolution image in response, and if the command specifies a higher frame rate, the sensing device 300 may output a lower-resolution image at an increased frame rate.

The sensing device 700 (e.g., the functional unit 704) may also be configured to receive ad hoc commands through the programming/calibration API 718. Such ad hoc commands may include, for example, a command to zoom in or zoom out a sensor, a command to reset the sensing device 700 (e.g., restart the device or reset one or more operating parameters of the device to default values), a command to enable or disable a specific functionality of the sensing device 700, etc. The sensing device 700 (e.g., the functional unit 704) may also be programmed and/or trained (e.g., over a network) via the programming/calibration API 718. For example, the sensing device 700 may receive training data and/or operating logics through the programming/calibration API 718 during and/or after an initial configuration process.

The sensing device 700 and/or the functional unit 704 may be configured to be modular and extensible such that sensors, communication circuits, data processing devices, computation units, and/or data rendering units may be added to or removed from the sensing device 700, for example, to accommodate different system settings, configurations and/or requirements in a medical environment. For example, if output quality is the priority in the medical environment, a high-resolution sensor (e.g., a high-resolution camera) may be included in (e.g., added to) the sensing device 700 to satisfy the priority. On the other hand, if the priority is on output speed (e.g., frame rate), a sensor (e.g., a camera) with lower resolution and/or a communication circuit with faster bitrates (e.g., an ethernet card rather than a WiFi card) may be used to meet the output requirement. As another example, the sensing device 700 may be configured to work (e.g., simultaneously) with multiple devices in the medical environment such as multiple imaging modalities (e.g., CT, MR, etc.), in which case the sensing device may include respective sets of sensors, communication circuits, power supplies, processors (e.g., data processing devices, computation units, and/or data rendering units as described herein) for the respective medical devices. As yet another example, the sensing device 700 may be configured to receive images of multiple patients (e.g., from different sensors) and generate respective 2D or 3D models for the patients based on the images, for example, simultaneously. In such a scenario, the sensing device 700 may include respective sets of sensors, communication circuits, power supplied, processors (e.g., data processing devices, computation units, and/or data rendering units as described herein) for capturing and processing the respective images of the respective patients.

In examples, the sensing device 700 and/or the functional unit 704 may comprise multiple slots (e.g., expansion boards, etc.) each equipped with at least one of a power connector or a communication circuit (e.g., a network interface card, a USB port, etc.) capable of transmitting and receiving information over a wired or wireless communication link. Sensors and/or processors (e.g., data processing devices, computation units, and/or data rendering units as described herein) may be hosted in (e.g., inserted into) these slots, upon which the sensors and/or processors may receive power through the respective power connectors and perform data exchange with one or more internal or external devices via the respective communication circuits. These sensors and processors may respectively possess similar capabilities as the sensor 702, the data processing device 710, the computation unit 712, and the data rendering unit 714 described herein, and may be added to or removed from the sensing device 700, for example, to accommodate changing conditions and/or requirements in the medical environment in which the sensing device 700 is installed. In this manner, the sensing device 700 may be modular and extensible to handle data processing tasks associated with different patients, devices, and/or imaging modalities. In other example situations such as when the amount of computation, communication, and/or data storage workload approaches or exceeds the capabilities of one set of sensors and/or processors, more of the sensors and/or processors may be added to share the workload.

Figure 8:
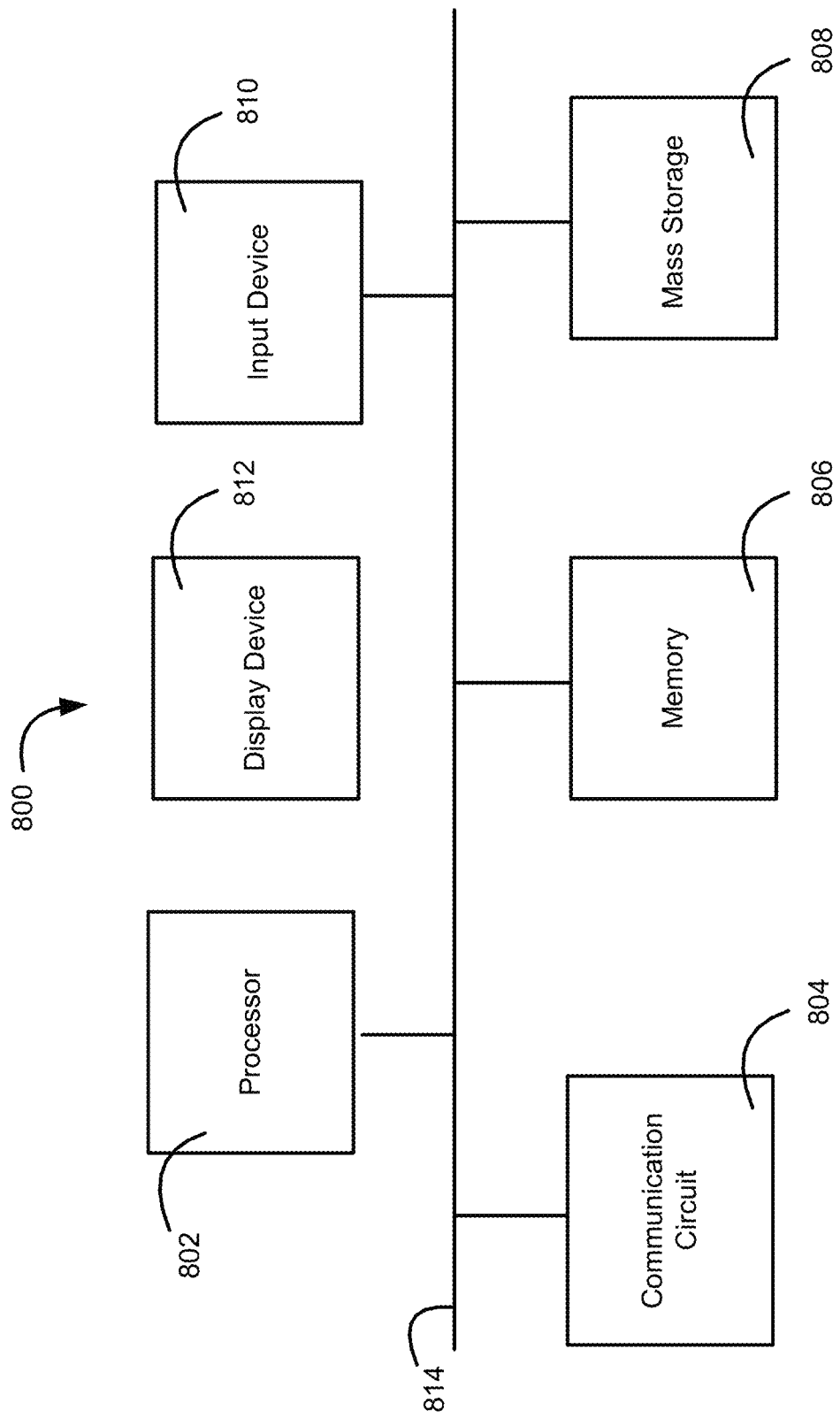
FIG. 8 a block diagram illustrating an example of a processing device described herein.

The processing device described herein (e.g., the processing device 112 of FIG. 1) described herein may be implemented using one or more processors, one or more storage devices, and/or other suitable accessory devices such as display devices, communication devices, input/output devices, etc. FIG. 8 illustrates example components of a processing device 800 as described herein. As shown, the processing device 800 may include a processor 802, which may be a central processing device (CPU), a graphics processing device (GPU), a microcontroller, a reduced instruction set computer (RISC) processor, application specific integrated circuits (ASICs), an application-specific instruction-set processor (ASIP), a physics processing device (PPU), a digital signal processor (DSP), a field programmable gate array (FPGA), or any other circuit or processor capable of executing the functions described herein. The processing device 800 may further include a communication circuit 804, a memory 806, a mass storage device 808, an input device 810, a display device 812, and/or a communication link 814 (e.g., a communication bus) over which the one or more components shown in FIG. 8 may exchange information. The communication circuit 804 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 806 may include a storage medium configured to store machine-readable instructions that, when executed, cause the processor 802 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 808 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 802. The input device 810 may include a keyboard, a mouse, a voice-controlled input device, a touch sensitive input device (e.g., a touch screen), and/or the like for receiving user inputs to the processing device 800. The display device 812 may include one or more monitors (e.g., computer monitors, TV monitors, tablets, mobile devices such as smart phones, etc.), one or more speakers, one or more augmented reality (AR) devices (e.g., AR goggles), and/or other accessories configured to facilitate the visual representation of contents on the display device 812. These contents may include, for example, information generated by the processing device such as a 3D mesh of a patient, simulated movements of a medical device, a plot of radiation exposure over time, etc. The display may be rendered in various formats including, for example, videos, animations, and/or AR presentations.

It should be noted that the processing device 800 may operate as a standalone device or may be connected (e.g., networked or clustered) with other computation devices to perform the functions described herein. And even though only one instance of each component is shown in FIG. 8, a skilled person in the art will understand that the processing device 800 may include multiple instances of one or more of the components shown in the figure. Furthermore, although example operations of the processing device may be depicted and described herein in a specific order, the operations may also take place in other orders, concurrently, and/or with other operations not presented or described herein. Not all operations that the processing device is capable of performing are depicted and described herein, and not all illustrated operations are required to be performed by the processing device.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A system for automating a medical environment, comprising:
   one or more sensing devices configured to capture images of the medical environment, wherein the one or more sensing devices include at least one of a camera, a depth sensor, or a thermal sensor, and wherein the images are associated with respective image coordinate systems and the medical environment is associated with a world coordinate system; and
   at least one processing device communicatively coupled to the one or more sensing devices and configured to:
      receive all or a subset of the images captured by the one or more sensing devices;
      identify one or more persons and one or more objects in the received images using a pre-trained image recognition neural network, wherein the one or more persons include a patient and the one or more objects include a medical device and an intermediate object located between the patient and the medical device;
      determine respective three-dimensional (3D) locations of the patient, the intermediate object, and the medical device in the medical environment based on respective positions of the patient, the intermediate object, and the medical device in the received images and respective spatial relationships between the world coordinate system and the image coordinate systems associated with the received images;
      generate, automatically, instructions for moving at least a part of the medical device towards the patient in accordance with the determined 3D locations of the patient, the intermediate object, and the medical device in the medical environment, wherein the instructions include navigation directions that prevent the part of the medical device from colliding with the intermediate object while the part of the medical device is moved towards the patient; and
      transmit the instructions to a receiving device.

2. The system of claim 1, wherein the instructions for moving at least the part of the medical device towards the patient further include navigation step sizes for moving at least the part of the medical device towards the patient and preventing the part of the medical device from colliding with the intermediate object.

3. The system of claim 2, wherein the instructions for moving at least the part of the medical device towards the patient include a plot that depicts a movement path of the part of the medical device towards the patient.

4. The system of claim 1, wherein the at least one processing device is further configured to determine a scan area or a surgical area of the patient based on the received images, and wherein the instructions are generated to move at least the part of the medical device towards the scan area or the surgical area of the patient.

5. The system of claim 4, wherein the at least one processing device is configured to generate a 3D parametric human model of the patient based on the received images and determine the scan area or the surgical area of the patient based on the 3D parametric human model.

6. The system of claim 1, wherein the one or more objects identified in the received images include a radiation source and the at least one processing device is further configured to determine, based on the received images, an orientation of the radiation source and a distance between the radiation source and the patient, the at least one processing device further configured to determine a radiation exposure of the patient based on the orientation of the radiation source and the distance between the radiation source and the patient.

7. The system of claim 1, wherein the at least one processing device is further configured to determine a current phase of a medical procedure being performed in the medical environment based on the one or more persons and the one or more objects identified in the received images.

8. The system of claim 7, wherein the at least one processing device is configured to acquire information indicating which persons and objects are associated with the current phase of the medical procedure and determine that the medical procedure is in the current phase based further on the acquired information.

9. The system of claim 1, wherein the respective 3D locations of the one or more persons and the one or more objects in the medical environment are indicated by respective coordinates of the one or more persons and the one or more objects in the world coordinate system and the respective positions of the one or more persons and the one or more objects in the received images are indicated by respective coordinates of the one or more persons and the one or more objects in the respective image coordinate systems associated with the received images.

10. The system of claim 1, wherein the at least one processing device is configured to determine the respective spatial relationships between the world coordinate system and the image coordinate systems based on images of one or more markers in the medical environment that are captured by the one or more sensing devices.

11. The system of claim 10, wherein the at least one processing device is configured to:
   determine respective coordinates of the one or more markers in the image coordinate system associated with each of the images of the one or more markers;
   determine respective coordinates of the one or more markers in the world coordinate system; and
   determine a rotation and a translation between the world coordinate system and the image coordinate system associated with each of the images of the one or more markers based on the respective coordinates of the one or more markers in the image coordinate system and the respective coordinates of the one or more markers in the world coordinate system.

12. The system of claim 1, wherein the one or more sensing devices include one or more two-dimensional (2D) cameras configured to capture 2D images of the medical environment or one or more three-dimensional (3D) cameras configured to capture 3D images of the medical environment.

13. The system of claim 12, wherein the at least one processing device is configured to determine respective depth locations of the patient and the medical device based on a first 2D image captured by a first 2D camera and a second 2D image captured by a second 2D camera.

14. The system of claim 1, wherein each of the one or more sensing devices comprises a communication circuit and is configured to communicate with at least another one of the one or more sensing devices via the communication circuit.

15. The system of claim 1, wherein the receiving device comprises the medical device or a control unit of the medical device.

16. The system of claim 1, wherein the medical device comprises an X-Ray scanner.

17. An apparatus configured to automate a medical environment, comprising at least one processor, wherein the at least one processor is configured to:
   receive a plurality of images of the medical environment captured by at least one of a camera, a depth sensor, or a thermal sensor;
   identify one or more persons and one or more objects in the received images using a pre-trained image recognition neural network, wherein the one or more persons include a patient and the one or more objects include a medical device and an intermediate object located between the patient and the medical device;
   determine respective three-dimensional (3D) locations of the patient, the intermediate object, and the medical device based on respective positions of the patient, the intermediate object, and the medical device in the received images and a respective spatial relationship between a world coordinate system associated with the medical environment and an image coordinate system associated with each of the received images;
   generate, automatically, a command for moving at least a part of the medical device towards the patient in accordance with the determined 3D locations of the patient, the intermediate object, and the medical device in the medical environment, wherein the instructions include navigation directions that prevent the part of the medical device from colliding with the intermediate object while the part of the medical device is moved towards the patient; and
   transmit the instructions to a receiving device.

18. A method for automating a medical environment, the method comprising:
   receiving images of the medical environment from one or more sensing devices, wherein the one or more sensing devices comprise at least one of a camera, a depth sensor, or a thermal sensor, and wherein the images are associated with respective image coordinate systems and the medical environment is associated with a world coordinate system;
   identifying one or more persons or one or more objects in the received images using a pre-trained image recognition neural network, wherein the one or more persons include a patient and the one or more objects include a medical device and an intermediate object located between the patient and the medical device;
   determining respective three-dimensional (3D) locations of the patient, the intermediate object, and the medical device based on respective positions of the patient, the intermediate object, and the medical device in the received images and respective spatial relationships between the world coordinate system and the image coordinate systems associated with the received images;
   generating, automatically, instructions for moving at least a part of the medical device towards the patient in accordance with the determined 3D locations of the patient, the intermediate object, and the medical device in the medical environment, wherein the instructions include navigation directions that prevent the part of the medical device from colliding with the intermediate object while the part of the medical device is moved towards the patient; and
   transmitting the instructions to a receiving device.

* * * * *